United States Patent [19]

Herweh et al.

[11] 4,384,094

[45] May 17, 1983

[54] 3-SUBSTITUTED-7-DIALKYLAMINO-SPIRO(2H-1-BENZOPYRAN-2,3'-(3H)-NAPHTHA(2,1-B)PYRANS)

[75] Inventors: John E. Herweh, Lancaster; Thomas B. Garrett, Lititz; Alan B. Magnusson, Lancaster, all of Pa.

[73] Assignee: Armstrong World Industries, Inc., Lancaster, Pa.

[21] Appl. No.: 313,731

[22] Filed: Oct. 22, 1981

[51] Int. Cl.$^3$ .................. C08F 234/02; C07D 311/96
[52] U.S. Cl. ...................................... 526/268; 549/344
[58] Field of Search ......................... 549/344; 526/268

[56] References Cited

U.S. PATENT DOCUMENTS

| | | | |
|---|---|---|---|
| 2,978,462 | 4/1961 | Berman et al. | 260/345.2 |
| 3,022,318 | 2/1962 | Berman et al. | 260/345.2 |
| 3,666,525 | 5/1972 | Kimura | 117/36.8 |
| 3,810,762 | 5/1974 | Laridon et al. | 96/48 R |
| 3,810,763 | 5/1974 | Laridon et al. | 96/48 R |
| 3,899,514 | 8/1974 | Baumann et al. | 260/345.2 |
| 3,971,808 | 7/1976 | Baumann et al. | 260/345.2 |
| 4,029,677 | 6/1977 | Baumann et al. | 260/345.2 |
| 4,110,348 | 8/1978 | Baumann et al. | 260/345.2 |
| 4,348,508 | 7/1982 | Herweh et al. | 549/344 |

FOREIGN PATENT DOCUMENTS 10740 5/1980 European Pat. Off. ......... 260/345.2

OTHER PUBLICATIONS

Feichtmayr et al., *Liebigs Ann. Chem.*, 1979(9), 1337–1345.

*Primary Examiner*—Nicky Chan
*Assistant Examiner*—C. Joseph Faraci

[57] ABSTRACT

Substituted spiro 2H-1-benzopyran-2,3'-(3H)-naphtho(2,1-b)pyrans particularly suitable for use as precursors to stable colored pyrylium salts are disclosed.

2 Claims, No Drawings

3-SUBSTITUTED-7-DIALKYLAMINO-SPIRO(2H-1-BENZOPYRAN-2,3'-(3H)-NAPHTHA(2,1-B)PYRANS)

This invention relates to substituted spiropyrans.

More specifically, this invention relates to spiro(2H-1-benzopyran-2,3'-(3H)-naphtho(2,1-b)pyrans).

Spiropyrans are of interest as precursors for the UV generation of colored pyrylium salts for use in applications as varied as dosimetry and optical data storage to the formation of non-contact decorative patterns (See S. Maslowski, "High Density Data Storage UV Sensitive Tape," Applied Optics, 13, No. 4, 857 (1974).

The present invention provides a novel type of substituted spiropyrans particularly suitable for use as precursors to stable colored pyrylium salts.

According to this invention there is provided a compound having the formula

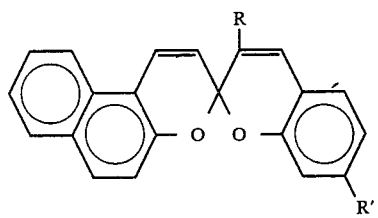

wherein R represents $C_1-C_{12}$ alkyl, alkylene aryl, aryl, unsaturated aryl, or cycloalkyl and R' represents dialkylamino.

The term "$C_1-C_{12}$ alkyl" is used in the specification and claims to signify a straight or branched alkyl group containing from 1 to 12 carbon atoms, with no more than 6 carbon atoms in its longest chain.

The term "aryl" is used in the specification and claims to signify phenyl or naphthyl, both of which may be unsubstituted or substituted in up to two positions with a substituent selected independently from $C_1-C_4$ alkyl, halo or $-NO_2$. "$C_1-C_4$ alkyl" is used above to signify a straight or branched alkyl group containing from 1 to 4 carbon atoms and "halo" is used above to signify fluoro, chloro, iodo and bromo.

The term "alkylene aryl" is used in the specification and claims to signify a moiety of the formula M—X—, wherein M represents aryl, as defined above, and X represents a straight or branched alkyl group having from 1 to 3 carbon atoms.

The term "unsaturated alkyl group" is used in the specification and claims to signify a straight or branched alkyl group containing at least 1 carbon-carbon double bond and having from 2 to 12 carbon atoms, with no more than 6 carbon atoms in its longest chain.

The term "cycloalkyl" is used in the specification and claims to signify saturated alkyl group having from 3 to 6 carbon atoms.

In the term "dialkylamino," as used herein, each alkyl substituent is independently selected from a straight or branched alkyl group containing from 1 to 4 carbon atoms.

The novel substituted spiropyrans of this invention are prepared by the acid-catalysed condensation of 4-dialkylamino salicylaldehyde with the appropriately substituted methyl ketone to form a substituted styryl ketone intermediate which is not isolated. 2-Hydroxynaphthaldehyde is then added to the reaction mixture to thereby produce the desired substituted spiropyrans.

Substantially equimolar amounts of the substituted methyl ketone, the 4-dialkylamino salicylaldehyde and the 1-hydroxynaphthaldehyde are utilized in the process, which proceeds according to the following reaction formula:

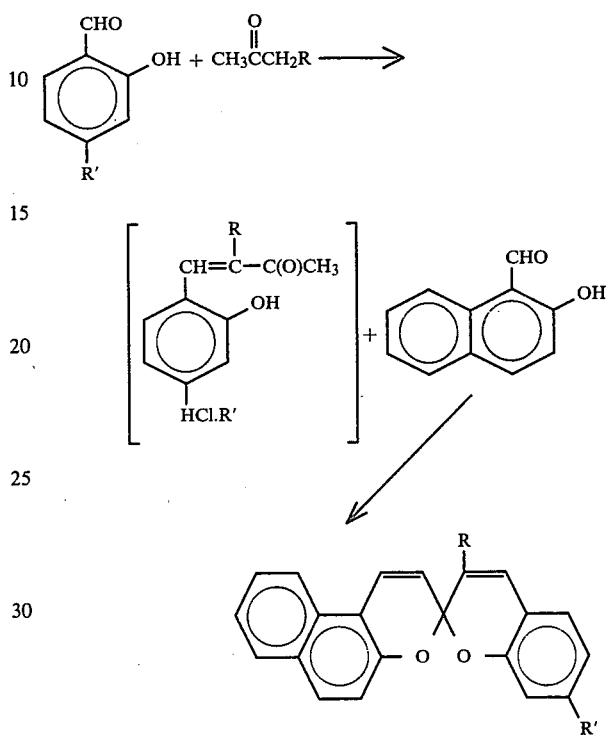

wherein R and R' are as defined above.

The substituted methyl ketones utilized herein are available commercially or can be prepared by using the procedures as set forth in *Organic Functional Group Preparation*, S. R. Sandler and W. Karo, Academic Press, New York, p. 169 and *Synthetic Organic Chemistry*, R. B. Wagner and H. D. Zook, New York, Wiley and Sons, Inc., p. 339.

The spiropyrans of this invention will react with photogenerated protic acids to form colored pyrilium salts. In this well-known method the protic acids, which are typically hydrogen halides, are generated by light within a substrate containing the spiropyran. Precursors for the hydrogen halides are typically tri halo alcohols, i.e., 2,2,2-tribromoethanol, which absorb light and generate hydrogen halides which react with the spiropyran to give a colored salt.

The stability of the colored pyrylium salts resulting from interaction of photogenerated protic acids with the spiropyrans is important. It is known that the nature of ring substitution (see rings A and B, equation 2 below) can influence stability. (G. Arnold, G. Paal, and H. P. Vollmer, Z. Naturforsch, B 25 (12), 1413 (1970); U.S. Pat. No. 3,733,197 to C. Schiele.)

Further, it has now been found that the substitution at the 7-position of ring B below of an π electron-donating group (e.g. dialkylamino) is effective in stabilizing the color of pyrylium salts. The compounds of this invention have been found to be particularly effective in this respect.

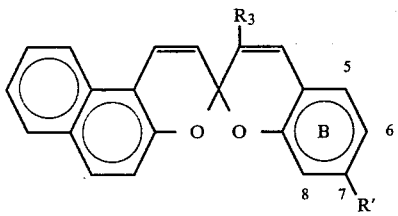

It has also been discovered that the spiropyrans of this invention in which R is an unsaturated alkyl group, may be copolymerized with acrylates via a free radical process which utilizes well known initiators such as, for example, azobis (isobutyronitrile) and 2,2'-azobis(2-methylpropionitrile). The resulting copolymers are precursors to chromogenic materials that find varied application from optical data storage to the formation of noncontact decorative patterns.

The term "acrylates" as used herein refers to acrylates and methacrylates that have the formula:

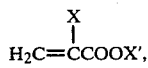

wherein X is H or $CH_3$ and X' is H or a straight or branched alkyl group having from 1 to 12 carbon atoms.

Reference is now made to the following example which is provided to illustrate but not to limit the practice of this invention.

EXAMPLE

Preparation of 3-methyl-7-dimethylamino-2,2'-spiro(2H-1-benzopyran-2,3'-(3H)-naphtho(2,1-b)pyran)

To a solution of 4-dimethylamino salicylaldehyde (5.45 g, 0.033 mol) and methyl ethyl ketone (2.4 g, 0.033 mol) in 12 ml of glacial acetic acid cooled in ice water there was added anhydrous hydrogen chloride. The addition of hydrogen chloride was made below the liquid surface for a period of 75 min. To the resulting magenta colored reaction mixture there was added a solution of 2-hydroxynaphthaldehyde (5.68 g, 0.033 mol) in 15 ml of glacial acetic acid. The addition of hydrogen chloride was resumed as before, while the reaction mixture was cooled at ice water bath temperature. After ca. 150 min, the passage of hydrogen chloride was terminated and the reaction was stopped and set aside.

After ca. 16 hrs. the intensely colored (deep magenta) reaction mixture formed a gelatinous mass. The latter was slurried with 200 ml of ether, and the resulting two-phase mixture was separated by decanting the liquid ether phase. Ether (200 ml) was added to the highly colored ether insoluble semi-solid and after slurrying, again gave two phases. The ethereal layer was decanted, and the ether insoluble residue dried in vacue. The resulting bluish-green gummy solid was slurried with 200 ml of acetone and dilute ammonium hydroxide was added until the mixture was weakly alkaline.

The resulting dark amber reaction mixture was filtered, and the filtrate (two-phases) was concentrated on a Rota-vap. The dark residue was treated with ether, and the dark amber ethereal phase separated and dried over anhydrous magnesium sulfate. The dried ethereal solution was concentrated to dryness under reduced pressure and left an iridescent green solid residue (7.1 gm). Recrystallization of this crude reaction product from benzene-hexane and subsequently from hexane alone gave the desired product. The product sintered and shrank at 130°–40° and carbonized at 152°–6°. Anal. Calcd. for $C_{24}H_{21}NO_2$: C, 81.1; H, 6.0; N, 3.9. Found: C, 80.6; H, 6.1; N, 3.6. UV (THF) 308 nm (24,470).

The NMR assignments of the desired product summarized below.

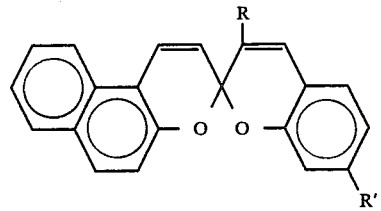

| Proton | $H_A$ | $H^B$ | $H_C$ | $H_D$ & $H_E$ |
|---|---|---|---|---|
| Chemical* shifts, ppm, | 2.79(s) | 1.97(s) | 6.05(d) | in aromatic |
| | | | Aryl protons 6.1–8.2 | |

*In $CDCl_3$ solvent, TMS as internal standard.

What is claimed is:

1. A spiropyran compound having the formula

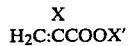

wherein R represents unsaturated alkyl and R' represents dialkylamino.

2. A copolymer produced by the free radical polymerization of a spiropyran compound of claim 1 and an acrylate of the formula $$H_2C:CCOOX'$$
     X wherein X is H or $CH_3$ and X' is H or a straight or branched alkyl group having from 1 to 12 carbon atoms.

* * * * *